US012734272B2

(12) United States Patent
Athalin et al.

(10) Patent No.: US 12,734,272 B2
(45) Date of Patent: Sep. 15, 2026

(54) ECOBIOLOGICAL TREATMENT OF SIDE EFFECTS OF RADIOTHERAPY

(71) Applicant: BIONUCLEI, Aix en Provence (FR)

(72) Inventors: Han Athalin, Nantes (FR); Jean-Noël Thorel, Paris (FR)

(73) Assignee: BIONUCLEI, Aix en Provence (FR)

( * ) Notice: Subject to any disclaimer, the term of this patent is extended or adjusted under 35 U.S.C. 154(b) by 1254 days.

(21) Appl. No.: 17/627,472

(22) PCT Filed: Jul. 17, 2020

(86) PCT No.: PCT/EP2020/070323
§ 371 (c)(1),
(2) Date: Jan. 14, 2022

(87) PCT Pub. No.: WO2021/009360
PCT Pub. Date: Jan. 21, 2021

(65) Prior Publication Data

US 2022/0401618 A1 Dec. 22, 2022

(30) Foreign Application Priority Data

Jul. 18, 2019 (FR) ...................................... 1908136

(51) Int. Cl.
*A61L 26/00* (2006.01)
*A61K 31/738* (2006.01)

(52) U.S. Cl.
CPC .......... *A61L 26/008* (2013.01); *A61K 31/738* (2013.01); *A61L 26/0004* (2013.01); *A61L 26/0052* (2013.01); *A61L 2300/232* (2013.01); *A61L 2300/404* (2013.01); *A61L 2300/802* (2013.01); *A61L 2430/34* (2013.01)

(58) Field of Classification Search
CPC ............... A61L 26/008; A61L 26/0004; A61L 26/0052; A61L 2300/232; A61L 2300/404; A61L 2430/34; A61L 2300/802; A61K 31/738
See application file for complete search history.

(56) References Cited

U.S. PATENT DOCUMENTS

2010/0074932 A1* 3/2010 Talsma ................. A61K 33/244 427/430.1
2016/0030476 A1* 2/2016 Vachon ................ A61K 31/737 424/641
2021/0251861 A1 8/2021 Thalin et al.

FOREIGN PATENT DOCUMENTS

EP 3466454 A1 4/2019
WO 2019/229401 A1 12/2019

OTHER PUBLICATIONS

Schindewolf, Marc, et al. "Incidence and causes of heparin-induced skin lesions." Cmaj 181.8 (2009): 477-481. (Year: 2009).*
Wong, Stalia, and Chirk-Jenn Ng. "A skin lesion and fever of unknown origin: A case study." Australian Family Physician 41.1/2 (2012): 41-44. (Year: 2012).*
Spalek, Mateusz. "Chronic radiation-induced dermatitis: challenges and solutions." Clinical, cosmetic and investigational dermatology (2016): 473-482. (Year: 2016).*
Venes, Donald. Taber's cyclopedic medical dictionary. FA Davis, 2017, portion of p. 1919. (Year: 2017).*
Nunamaker, Elizabeth A., Erin K. Purcell, and Daryl R. Kipke. "In vivo stability and biocompatibility of implanted calcium alginate disks." Journal of Biomedical Materials Research Part A. 83.4 (2007): 1128-1137. (Year: 2007).*
Motoyama, Keiichi, et al. "Anti-inflammatory effects of novel polysaccharide sacran extracted from cyanobacterium Aphanothece sacrum in various inflammatory animal models." Biological and Pharmaceutical Bulletin 39.7 (2016): 1172-1178. (Year: 2016).*
Fraser-Pitt, Douglas J., et al. "Cysteamine . . . bacterial infection." Infection and Immunity 86.6 (2018): 10-1128. (Year: 2018).*
Cornwell, Daniel J., Oliver J. Daubney, and David K. Smith. "Photopatterned multidomain gels: multi-component self-assembled hydrogels based on partially self-sorting 1, 3: 2, 4-dibenzylidene-D-sorbitol derivatives." Journal of the American Chemical Society 137.49 (2015): 15486-15492 and SI. (Year: 2015).*
Draper, Emily R., et al. "Spatially resolved multicomponent gels." Nature chemistry 7.10 (2015): 848-852. (Year: 2015).*
Draper, Emily R., and Dave J. Adams. "How should multicomponent supramolecular gels be characterised?." Chemical Society Reviews 47.10 (2018): 3395-3405. (Year: 2018).*
International Search Report (and English Translation) and Written Opinion for PCT/EP2020/070323, mailed Dec. 8, 2020.

* cited by examiner

*Primary Examiner* — Scarlett Y Goon
*Assistant Examiner* — David H Cho
(74) *Attorney, Agent, or Firm* — HESLIN ROTHENBERG FARLEY & MESITI P.C.

(57) ABSTRACT

The present invention concerns a three-dimensional bipolymeric matrix deploying biological and biomechanical activity, able to neutralize the various physiopathological parameters involved in the development and worsening of skin lesions and/or sores, combining:

- a first polymeric network comprising first colloids (Col-1) bonded non-covalently to an unsulfated crosslinked polysaccharide; and
- a second polymeric network comprising second colloids (Col-2) bonded covalently or non-covalently to a sulfated polysaccharide.

20 Claims, 2 Drawing Sheets

[Fig. 1]
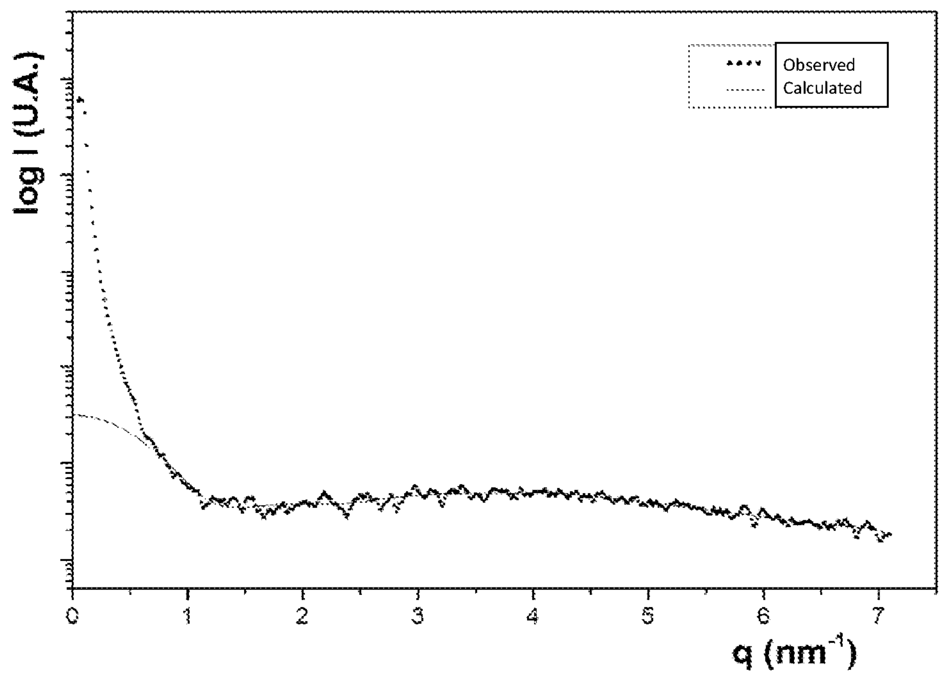
[Fig. 2]
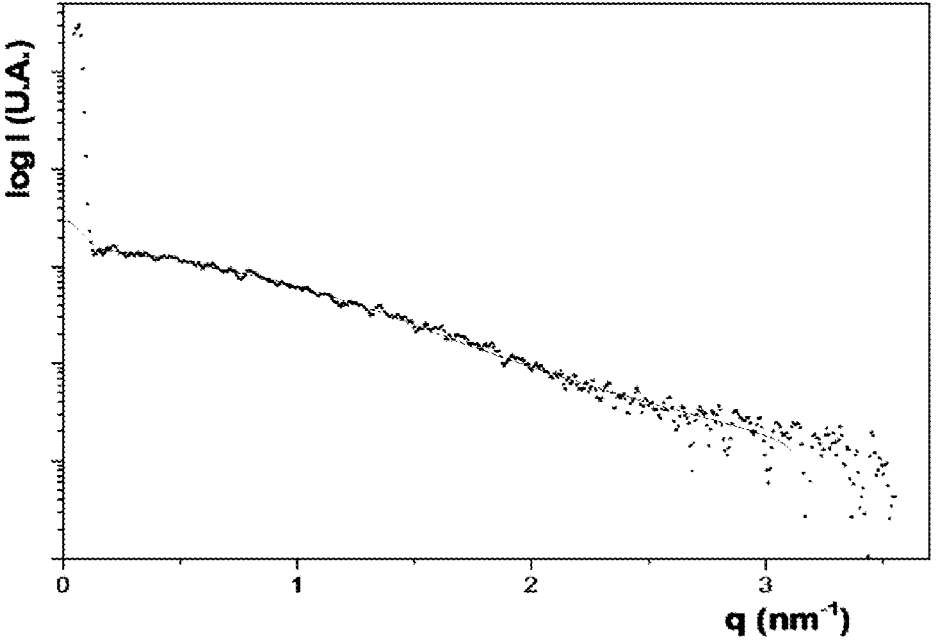

[Fig. 3]
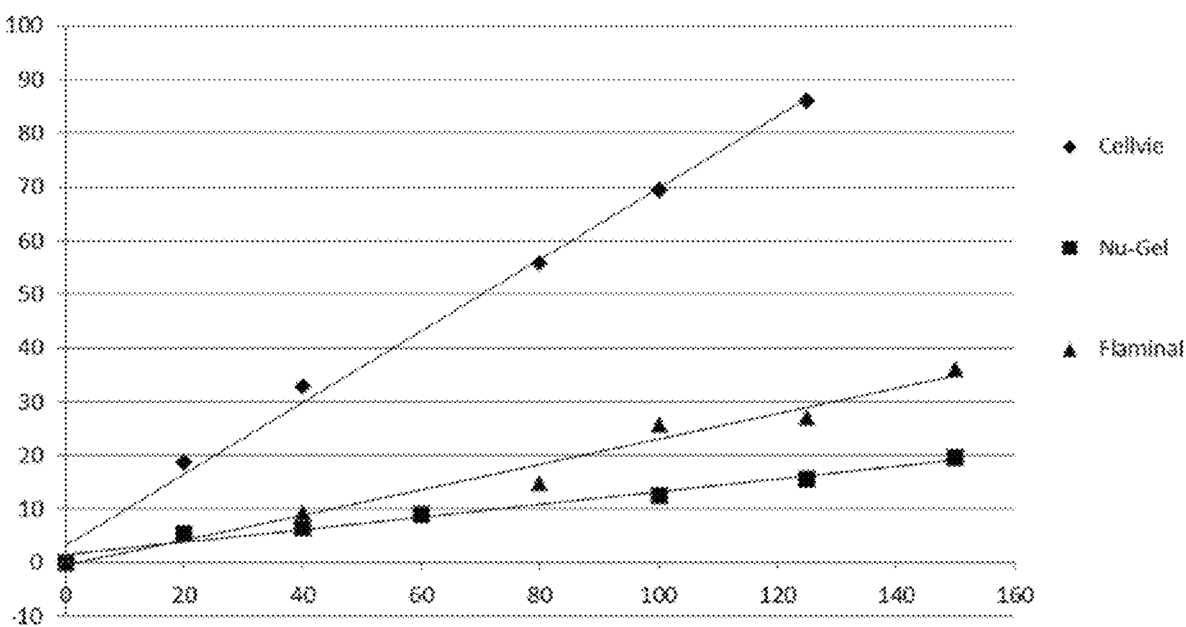

ECOBIOLOGICAL TREATMENT OF SIDE EFFECTS OF RADIOTHERAPY

CROSS REFERENCE TO RELATED APPLICATIONS

This application is a national stage filing under section 371 of International Application No. PCT/EP2020/070323, filed on Jul. 17, 2020, and published on Jan. 21, 2021 as WO 2021/009360, which claims priority to French Application No. 1908136, filed on Jul. 18, 2019. The entire contents of WO 2021/009360 are hereby incorporated herein by reference.

FIELD OF THE INVENTION

The present invention relates to a three-dimensional bipolymeric matrix deploying biomechanical activity, able to neutralize the various physiopathological parameters involved in the development and worsening of skin lesions and/or sores, in particular radiodermatitis.

PRIOR STATE OF THE ART

According to the latest estimates published by the International Agency for Research on Cancer on the basis of data collected in 185 countries, 18.1 million new cases of cancer were diagnosed worldwide in 2018.

In France, the global number of new cancer cases has been increasing every year for 30 years. This is mainly due to the aging of the population and the improvement of diagnostic methods. In 2017, there were an estimated 400,000 new cases of cancer in metropolitan France according to the National Cancer Institute.

It follows that cancer remains a major public health problem in France and around the world.

Depending on the nature of the tumor, its molecular profile and/or its location, numerous treatments are implemented to limit or stop the progression of the disease. Whether performed alone or in combination within the framework of multidisciplinary care, a classic distinction is made between surgery, radiotherapy, immunotherapy, hormone therapy, targeted therapies or chemotherapy.

These treatments are particularly aggressive on the body and are usually accompanied by side effects.

In particular, radiation therapy (or irradiation) involves the use of high-energy rays to destroy or damage cancer cells. The main biological effect of ionizing radiation is to break down DNA strands in tumor cells, either directly or through the formation of free radicals, resulting in the death of these cells.

However, exposure to ionizing radiation induces the onset of side effects such as radiodermatitis. These are skin lesions, the severity of which is classified in grades according to the international classification "Common Terminology Criteria for Adverse Events":

- Grade 1: Erythema occurring within a few days up to three weeks after the radiotherapy session, especially in subjects with a light skin phototype. It is often accompanied by smarting sensations and edema. It is frequent but regresses rapidly when treatment is stopped, after a desquamation phase and, often, transient hair loss caused by damage to the skin appendages (hair follicles, sweat glands or sebaceous glands).
- Grade 2: Erythema and edema of moderate intensity, limited exudative plaques at the irradiation site.

- Grade 3: Exudative radiodermatitis which usually follows erythema when irradiation is pursued. It is characterized by detachments and confluent ulcerations leaving the dermis bare several weeks after irradiation. Epithelialization (or reconstruction of the epithelium) takes place over a few weeks to several months depending on the site of the lesion, resulting in dyschromia and alopecia, most often permanent. Radiation therapy must usually be stopped to enable time for healing.
- Grade 4: acute radionecrosis which attests to an overdose, currently exceptional except in the case of very extensive surface or infiltrating tumors (massive irradiation in a very short time). It appears within days as a very painful inflammatory patch with necrotic and hemorrhagic phenomena progressing to deep necrosis, which can expose muscles, tendons and bones.

Therefore, ranging from simple erythema sicca to tissue necrosis, through a more or less exudative intermediate phase, radiodermatitis is not the subject of any particular treatment protocol. As numerous as they are varied, the treatments commonly used to treat this type of skin lesions are similar to those used in the event of burns (emollients, dermocorticoids, dressings such as Vaseline gauze, hydrogels, hydrocolloids or even charcoal or silver-coated dressings).

The choice of the best treatment depends directly on the type of lesion to be treated, namely, dry, oozing, heavily exudative, infected etc. For example, a hydrogel-type dressing is likely to promote healing of a dry lesion, keeping it in a moist environment. On the other hand, its application to an exudative radiodermatitis is likely to lead to a phenomenon of maceration which then inhibits healing and which may cause an infection or superinfection.

More generally, the skin can be damaged by means other than the ionizing radiation from radiation therapy.

A skin sore or lesion is an interruption in the continuity of tissue. There is a wound when the skin or the mucous membrane is broken, cut or torn off. The severity of the sore is characterized by its location, appearance and origin (burn, bite, cut, etc.).

Skin lesions can be classified based on biological and clinical characteristics such as the need for hydration/nutrition and the need for occlusion. It is possible to distinguish 3 families of lesions:

- Oozing lesions: these are lesions subject to maceration that require drying with non-occlusive care in order to allow air to pass. These include, for example, diaper rash, maceration of folds, chickenpox with oozing lesions or blisters.
- Type I non-oozing lesions: these are superficial to medium-sized lesions that need hydration with semi-occlusive, breathable care. These include, for example, stitches, cuts, abrasions of everyday life after the sores have dried, chickenpox in the healing phase, lesions following an aesthetic act (peeling, laser, permanent hair removal, tattooing, tattoo removal, etc.) or non-oozing diaper rash.
- Type II non-oozing lesions: these are medium to major lesions which require lipid-replenishing nutrition with occlusive care to create a barrier to the external environment. These include, for example, chapped skin, sores, pulpitis, burns or excoriations.

The skin isolates and protects the body against the external environment. When a sore occurs, the body triggers a natural biological phenomenon: healing. It is a complex repair process in which the body must stop possible bleeding, protect, cleanse and close the wound. The damaged tissue must be reconstituted, as close as possible to the initial tissue.

The natural healing process of a lesion is a succession of biochemical, biological and cellular stages, all of which are essential for healing.

Healing may be defined as a phenomenon comprising 3 successive phases, characterized by specific cellular activities, which advance the repair process according to precise chronological sequences which overlap with each other:

- Stage 1—inflammatory or debridement phase: Immediately after the lesion has formed, the local blood vessels dilate causing increased vascular permeability and plasma leakage. This vasodilation is followed shortly after by vasoconstriction and then by the formation of clots at the bottom of the lesion thanks in particular to the action of platelets, which limits blood loss. Later, attracted by chemotactic substances, pro-inflammatory cells (leukocytes and macrophages) arrive from surrounding tissues to cleanse the lesion, eliminating dead tissue, germs and bacteria. This phase begins between the 12th and 24th hour and causes an inflammatory reaction characterized by redness (erythema), swelling (edema), pain and an increase in local temperature.

Although necessary, it is important that this inflammatory state does not last longer than three days, otherwise the subsequent stages of cell proliferation and new epithelial formation or (epithelialization) may be delayed. However, in some cases, inflammation can be stimulated and prolonged by the presence of free radicals such as reactive nitrogen species (RNS) and reactive oxygen species (ROS). These compounds will naturally induce oxidation of the newly synthesized biomolecules in the lesion and therefore slow down the process of cell regeneration and healing.

- Stage 2: Budding or granulation tissue formation phase: During this phase, connective tissue cells, fibroblasts, appear in large quantities after stimulation and recruitment by macrophages. Fibroblasts produce significant amounts of collagen, elastin and other elements of the cell matrix of the dermis. At the same time, endothelial cells form buds at the ends of damaged capillaries. This overgrowth stops when the granulation tissue has filled in the loss of substance and the fibroblasts have reached the edges of the lesion.
- Step 3: Epidermization or epithelialization phase: Once the primary scar has formed, around the 25th or 30th day, the collagen begins to deteriorate significantly and marks the start of remodeling of the primary scar. During this phase, the lesion edges continue to contract slowly thanks to the action of myofibroblasts and the strengthening of the junction between the epidermis and the dermis. The result is that, little by little, the scar becomes more flexible, smoother and softer to the touch. This remodeling results in the formation of the final scar after 6 months to a year or more.

The quality of the final scar depends on its size, its location and especially the initial progress of healing, hence the importance of care and follow-up during the formation of the primary scar.

An alteration in the primary healing process of an acute lesion may lead to the formation of a chronic and complicated lesion requiring specialized care with dressings and materials allowing so-called "directed" healing, or to the formation of an abnormal scar, unsightly which may even present functional sequelae.

A lesion that is not treated properly presents a significant risk of infection, which, in turn, affects the healing process. The term "contamination" is used when the damaged tissue is populated with bacteria, which do not yet multiply. In contrast, the "colonization" phase involves bacterial proliferation within the lesion. Colonization may turn into "critical colonization" and then into local infection of the lesion. The bacteria then penetrate deeper into the damaged tissue and multiply there, causing inflammatory reactions. The general symptoms of such an infection are fever, rash, pain in the lesion area, or leukocytosis. Through the bloodstream, the local infection may develop into a "systemic infection" and spread throughout the body, possibly developing into acute sepsis which can lead to the death of the subject.

In the field of wound care, the choice of the dressing makes a decisive contribution to guaranteeing its therapeutic effectiveness and carrying out the care under the required sterile conditions.

It clearly appears that the choice of the best treatment depends directly on the type of wound to be treated. To achieve maximum effectiveness a dressing should ideally combine many features and functions such as being able to prevent the risk of infection, absorb excess exudate and blood, create or maintain a moist environment around the lesion, facilitate the migration of leukocytes, maintain good thermal insulation or be breathable.

Today, such a spectrum of features is not found in a single dressing. It is necessary to adapt the dressing to the type of lesion, or even to change it as the healing stages progress.

Therefore, there remains a clear need to develop a unique dressing capable of treating with maximum efficiency all types of skin lesions and/or severity grades of a lesion, in particular radiodermatitis.

DISCLOSURE OF THE INVENTION

The applicant has observed that a three-dimensional bipolymeric matrix makes it possible to organize and control the conditions essential for the healing of a lesion (humidity, temperature, pH, oxygenation), whatever the type of lesion, its state of development and/or its state of healing.

The present invention solves the problems of the prior art discussed above.

According to a first aspect, the invention relates to a three-dimensional bipolymeric matrix deploying biomechanical activity, capable of neutralizing the various physiopathological parameters involved in the development and aggravation of skin lesions and/or wounds combining:

- a first polymeric network comprising first colloids (Col-1) bonded non-covalently to an unsulfated crosslinked polysaccharide; and
- a second polymeric network comprising second colloids (Col-2) bonded covalently or non-covalently to a sulfated polysaccharide.

For the purposes of the invention, the term "colloid" is understood to mean crystalline particles (non-amorphous form) resulting from the ordered stack of molecules which constitute them. These colloids may also be called "quantum dots" or nanocrystals. They may be in the form of a suspension of colloids in an aqueous medium.

The notion of bonding of Col-1 and Col-2 colloids is part of the general knowledge of a person skilled in the art. Bonding is the formation of non-covalent bonds or covalent bonds.

Naturally, non-covalent or covalent bonding is not limited to the bonding of a single compound. Possibly, it is the bonding of a multitude of molecules of at least one type of compound on each nanocrystal.

The formation of the Col-2/sulfated polysaccharide complex is carried out according to the knowledge of a person skilled in the art, in particular the formation of a covalent or non-covalent bond.

In a particular embodiment, the second colloids (Col-2) are covalently bonded to the sulfated polysaccharide.

For example, the sulfated polysaccharide may be modified by adding thiol groups (R—S—H). When the Col-2 colloids are placed in the presence of the sulfated polysaccharide modified by adding thiol groups, covalent bonds are formed between the sulfur atoms (S) of the thiol groups carried by the sulfated polysaccharide and the metal molecules constituting the colloids Col-2.

In a preferred embodiment, the second colloids (Col-2) are non-covalently bonded to the sulfated polysaccharide.

For example, the Col-2 colloids may be surface and covalently bonded with an agent capable of positively charging the colloid, preferably cysteamine, which makes it possible to establish non-covalent electrostatic interactions between the second colloids (Col-2) and the negatively charged sulfated polysaccharide.

For the purposes of the invention, the term "positively charged" and "negatively charged" are understood to mean the charge presented on the surface of colloids at neutral, physiological or acidic pH (pH 3-7).

Colloids can be synthesized according to conventional techniques, for example by the so-called "bottom-up" approach of growth of precursors. This synthetic route, commonly used in the field of nanomaterials, involves a nucleation step and a growth step from isolated atoms. It makes it possible to control the size of the colloids.

Col-1 and Col-2 colloids are different from each other, that is, they are made up of at least one different chemical element. Indeed, they do not have the same properties.

According to a particular embodiment, the Col-1 colloids consist of a chemical element chosen from the group comprising Ce, Si, Ge, Sn, Te, B, N, P, As, Al, Sb, Ga, In, Cd, Zn, Cu, Cl, Pb, Tl, Bi, Ti, U, Ba, Sr, Li, Nb, La, I, Mo, Mn, Ca, Fe, Ni, Eu, Cr, Br, Ag, Pt, Hg, and their assemblies.

According to a particular embodiment, the Col-2 colloids consist of a chemical element, preferably a metal, preferably chosen from the group comprising Pt, Au, Ni, Cu, Pd and Ag.

According to a particular embodiment, the metal constituting the Col-2 colloids exhibits a zero oxidation state.

According to a particular embodiment, the Col-1 colloids according to the invention are cerium dioxide ($CeO_2$) colloids.

According to a particular embodiment, the Col-2 colloids according to the invention are platinum (Pt) colloids.

Preferably, the Col-2 colloids have amine groups at their surface.

For the purposes of the invention, Col-2 colloids have a core made of a metal, while they have a surface covalently or non-covalently bonded to a sulfated polysaccharide. This is a core/surface type notion. The term "core" is not to be associated with a core/shell type structure.

The surface of Col-2 colloids may optionally have an oxide layer. In this case, the colloids have a metal core and an oxide surface, which is covalently bonded to a sulfated polysaccharide.

Preferably, the Col-1 colloids are cerium dioxide ($CeO_2$) colloids and the Col-2 colloids are platinum (Pt) colloids with zero oxidation state, preferably platinum whose core exhibits zero oxidation state.

In general, Col-1 colloids and/or Col-2 colloids have an average size of the order of a few nanometers to a few tens of nanometers.

Thus, the Col-1 colloids and/or the Col-2 colloids according to the invention have a size preferably between 0.1 nm and 1000 nm, more preferably between 0.3 nm and 100 nm, and even more preferably less than 10 nm, or even less than 5 nm, the size being preferably measured by XRD.

Preferably, the size of Col-1 colloids is between 0.4 nm and 2 nm.

Preferably, the size of Col-2 colloids is between 1 and 5 nm, preferably between 2 and 3 nm.

X-ray diffraction (XRD) is a technique conventionally used to measure the size of crystals in the solid state.

The term "size" is understood to mean the largest dimension of the Col-1 and Col-2 colloids, for example the diameter in the case of Col-1 and Col-2 colloids of spherical shape. It refers to the number average size of non-covalently bonded Col-1 colloids and covalently bonded Col-2 colloids. However, the size of the colloids prior to the non-covalent or covalent bond, optionally coated with a polymer such as dextrose, myo-inositol or polyvinylpyrrolidone (PVP), is also included in the ranges of values indicated above. Where appropriate, a person skilled in the art will be able to adapt the size of the unbound $CeO_2$ colloids and the unbound Pt colloids.

The coating of the colloids according to the invention makes it possible to control their growth during their formation. For example, in a Col-1/dextrose or Col-1/myo-inositol complex, dextrose and myo-inositol play a role in controlling the size of the Col-1 particles during their formation.

For the purposes of the invention, the term "control of the growth of colloids" is understood to mean the mechanism by which the size of the colloids is smaller and less polydispersed, that is to say, that all the particles have sufficiently close sizes when forming a narrow distribution around the average.

The colloids according to the invention are preferably of spherical shape.

The colloids are not doped. Optionally, they may comprise an element, preferably a transition metal, which is introduced during the synthesis of the colloids.

According to a particular embodiment, the unsulfated polysaccharide according to the invention has a molecular mass of between 1 kDa and 5 million Dalton (MDa), preferably between 5 kDa and 1 MDa.

According to a particular embodiment, the unsulfated polysaccharide according to the invention is chosen from the group comprising: alginate, hyaluronic acid, guar gum, xanthan gum, acacia gum, pullulan, dextran and their mixtures, preferably the alginate.

Preferably, the first polymeric network according to the invention is crosslinked by a crosslinking agent corresponding preferably to a metal, preferably a bivalent metal, even more preferably an alkaline earth metal, for example calcium or magnesium. This crosslinking agent is in particular calcium.

Preferably, the polymer network according to the invention corresponds to alginate crosslinked by means of a metal.

According to a particular embodiment, the crosslinking agent to unsulfated polysaccharide mass ratio is between 1 and 10, preferably between 1 and 4.

According to a particular embodiment, the Col-1 colloid to unsulfated polysaccharide mass ratio is between 1:50 and 1:1, preferably between 1:15 and 1:5, preferably the mass ratio is 1:10.

According to one embodiment, in the Col-1 colloid/unsulfated polysaccharide complex according to the invention, the Col-1 colloids are cerium dioxide colloids and the unsulfated polysaccharide is chosen from the group comprising: alginate, hyaluronic acid, guar gum, xanthan gum, acacia gum, pullulan, dextran and their mixtures, preferably alginate.

According to a particular embodiment, the sulfated polysaccharide according to the invention has a molecular mass of between 1 and 40 million Dalton (MDa), preferably between 5 and 30 MDa, preferably between 15 and 25 MDa.

According to a particular embodiment, the sulfated polysaccharide according to the invention is chosen from the group comprising the compound whose INCI designation is aphanothece sacrum polysaccharide; sulfated glycosaminoglycans, for example dermatan sulfate, heparin, heparan sulfate or chondroitin sulfate; glucans; fucans; fucoidans; carrageenans; ulvans, pentosan polysulfate and their mixtures, preferably aphanothece sacrum polysaccharide.

In a particular embodiment, the sulfated polysaccharide according to the invention is aphanothece sacrum polysaccharide (INCI) modified by adding thiol groups, before it is brought into contact with the Col-2 colloids.

Preferably, the second polymeric network according to the invention is crosslinked by Col-2 colloids, preferably platinum colloids with zero oxidation state, surface and covalently bonded with the compound corresponding to the INCI designation aphanothece sacrum polysaccharide modified by adding thiol groups.

In another particular embodiment, the Col-2 colloids, preferably platinum colloids with zero oxidation state, are surface and covalently bonded with an agent capable of positively charging the colloid, preferably cysteamine, which allows to establish non-covalent interactions between the amine groups of Col-2 and the sulphates of the sulfated polysaccharides according to the invention, preferably aphanothece sacrum polysaccharide (INCI).

In the two embodiments described above, the Col-2 colloids may act as a crosslinking agent.

According to a particular embodiment, the Col-2 colloid to sulfated polysaccharide mass ratio is between 1:50 and 1:1, preferably between 1:25 and 1:15, preferably the mass ratio is 1:20.

According to a particular embodiment, the ratio of non-covalently bonded Col-1 colloids to covalently or non-covalently bonded Col-2 colloids is between 30:1 and 2:1, preferably between 15:1 and 5:1.

According to one embodiment, in the Col-2 colloid/sulfated polysaccharide complex according to the invention, the Col-2 colloids are platinum colloids and the sulfated polysaccharide is chosen from the group comprising the compound whose INCI designation is aphanothece sacrum polysaccharide; sulfated glycosaminoglycans, for example dermatan sulfate, heparin, heparan sulfate or chondroitin sulfate; glucans, fucans, fucoidans, carrageenans, ulvans, pentosan polysulfate and their mixtures, preferably aphanothece sacrum polysaccharide.

According to a particular embodiment, the three-dimensional bipolymeric matrix according to the invention comprises water.

According to another particular embodiment, the Col-1 colloids, non-covalently bonded to an unsulfated polysaccharide, represent between 0.01% and 1% by weight of the bipolymeric matrix according to the invention, while the Col-2 colloids, covalently or non-covalently bonded to a sulfated polysaccharide, represent between 0.001% and 0.1% and water represents between 70% and 99%.

According to a particular embodiment, the bipolymeric matrix according to the invention contains:

- cerium dioxide colloids;
- alginate;
- calcium carbonate;
- zero oxidation platinum colloids, preferably platinum whose core exhibits zero oxidation state;
- polyvinylpyrrolidone;
- gluconic acid or gluconolactone, preferably gluconolactone;
- aphanothece sacrum polysaccharide (INCI) modified by adding thiol groups; and
- water.

According to a preferred embodiment, the bipolymeric matrix according to the invention contains:

- cerium dioxide colloids;
- alginate;
- calcium carbonate;
- zero oxidation platinum colloids, preferably platinum whose core exhibits zero oxidation state, modified by adding cysteamine;
- gluconolactone;
- aphanothece sacrum polysaccharide (INCI) and
- water.

According to another aspect, the invention relates to a matrix as defined above for use as a dressing to prevent and/or heal a skin lesion.

According to another embodiment, the skin lesion is dry or exudative.

According to another aspect, the invention relates to a matrix as defined above for use as a dressing for preventing and/or healing radiodermatitis.

According to another embodiment, the radiodermatitis is of dry to exudative grade.

In other words, these are grade 1, 2 or 3 radiodermatitis.

In particular, the bipolymeric matrix according to the invention corresponds to an entanglement of two crosslinked networks creating around the lesion an environment favorable to the prevention of the aggravation of said lesion and/or to an acceleration of its healing (humidity, temperature, pH, oxygenation, antibacterial functions and antioxidant functions).

Preferably, the bipolymeric matrix according to the invention corresponds to a matrix crosslinked by ionic bonds.

In the event of a lesion, the bipolymeric matrix according to the invention, for its use as a dressing, ensures a moist environment favorable to the speed and quality of healing. In particular, this moist environment is conducive to the division and migration of newly created cells during the epithelialization phase. Moisturizing the lesion also prevents the formation of a surface scab that slows complete healing and spare the patient certain detrimental side effects such as a mild depression at the site of the lesion.

In addition, the bipolymeric matrix, for its use according to the invention, makes it possible to maintain the lesion at a temperature close to body temperature, i.e., approximately 37° C., which ensures adequate proliferation of the keratinocytes and optimal conditions for carrying out the enzymatic reactions.

The bipolymeric matrix, for its use according to the invention, ensures that a pH between 7 and 7.6 is maintained, thus ensuring epithelial proliferation while limiting the proliferation of pathogenic organisms in the lesion.

The bipolymeric matrix, for its use according to the invention, acts as a physical barrier, role naturally assigned to the skin, but which the latter can no longer fulfill after having been injured. The dressing according to the invention provides oxygenation, that is to say, gas exchange between the lesion and the external environment, which is essential for healing.

The bipolymeric matrix, for its use according to the invention, has an effective, important, high absorbency power of the bleeding and exudates secreted by the lesion. Consequently, the dressing according to the invention does not have to be changed frequently and does not induce a disruption in the process of reconstruction of the epidermis.

According to the invention, the alginate and the compound corresponding to the INCI designation aphanothece sacrum polysaccharide allow absorption of fluids and exudates;

contribute to mechanical strength and elasticity and play an insulating role by maintaining the temperature and pH of the lesion.

At the same time, the complex formed by Col-1 colloids of $CeO_2$ non-covalently bonded to alginate, has an antioxidant role in controlling inflammation without completely inhibiting it. In other words, this complex makes it possible to eliminate, decrease or inhibit the synthesis of free radicals of the RNS and/or ROS type, the continuous synthesis of which could make the lesion chronic.

In addition, the complex formed by Col-2 colloids, preferably Pt Col-2 colloids, covalently or non-covalently bonded to aphanothece sacrum polysaccharide, has an antibacterial role.

The three-dimensional bipolymeric matrix according to the invention, for its use as a dressing, is more effective and more long-lasting in preventing and/or healing a skin lesion, in particular radiodermatitis.

The three-dimensional bipolymeric matrix according to the invention, for its use as a dressing, is also more economical due to fewer changes hence less traumatic for the lesion being treated due to the limited tearing of new epithelial cells in formation.

In addition, the three-dimensional bipolymeric matrix according to the invention, for its use as a dressing, offers a new alternative to the hospitalization of patients, whose progress in healing can now be monitored remotely by conventional means of telemedicine.

Indeed, and in an innovative manner, when the lesion is infected, the proliferation of the bacterial population leads to a variation in the pH, preferably an increase in the pH. There follows a change in the valence level of cerium. This results in a color change of the matrix from transparent to a color, for example orange, to indicate the need to change the dressing and/or to treat the lesion infection in order to ensure proper healing and reduce the risk of complications for the subject (sepsis, etc.).

Furthermore, the transparent structure of the bipolymeric matrix according to the invention makes it possible to allow a medical practitioner to easily observe the healing progress, possibly remotely, and to identify in real time any possible complications.

The three-dimensional bipolymeric matrix and the dressing according to the invention combine several characteristics and functions which allow them to:

- be non-toxic and non-allergenic;
- be able to effectively protect the lesion from the external environment;
- be able to prevent the risks of infection;
- be able to absorb excess exudates and blood;
- create or maintain a moist environment around the lesion;
- accelerate and improve healing;
- maintain good thermal insulation around the lesion to improve blood flow and migration of epidermal cells;
- be breathable and allow gas exchange between the lesion and its environment;
- maintain the pH at a level that promotes epithelial growth while limiting the proliferation of organisms in the lesion;
- be able to be easily removed without adhering to the lesion;
- offer an extended duration of use, i.e., to be more economical and less traumatic for the lesion;
- have an absorbent property intermediate between hydrogel and hydrocolloid dressings;
- be protective;
- be antioxidant; and
- be antibacterial.

According to another aspect, the invention relates to a process for producing a three-dimensional bipolymeric matrix as defined above using two solutions:

- a solution (A) comprising Col-1 colloids non-covalently bonded with an unsulfated polysaccharide, a source of bivalent metals, preferably an alkaline-earth metal, and Col-2 colloids bonded on the surface and non-covalently with a biocompatible polymer; and
- a solution (B) comprising an acidifier and a sulfated polysaccharide.

According to a preferred embodiment, the invention relates to a process for producing a three-dimensional bipolymeric matrix as defined above using two solutions:

- a solution (A) comprising Col-1 colloids non-covalently bonded with an unsulfated polysaccharide, a source of bivalent metals, preferably an alkaline earth metal, and Col-2 colloids surface and covalently bonded with an agent capable of positively charging the colloid, preferably cysteamine; and
- a solution (B) comprising an acidifier and a sulfated polysaccharide.

The bipolymeric matrix according to the invention is obtained by mixing solutions (A) and (B).

Preferably, the two solutions (A) and (B) are mixed in a proportion of 4/5 of solution (A) and 1/5 of solution (B).

According to a particular embodiment, in solutions (A) and (B) implemented in the method according to the invention:

- Col-1 colloids are cerium dioxide colloids;
- the unsulfated polysaccharide is alginate;
- the source of bivalent metals, preferably an alkaline earth metal, is a calcium salt, preferably calcium carbonate;
- Col-2 colloids are platinum colloids with zero oxidation state, preferably platinum whose core exhibits zero oxidation state;
- the biocompatible polymer is polyvinylpyrrolidone;
- the acidifier is gluconic acid or gluconolactone, preferably gluconolactone; and
- the sulfated polysaccharide corresponds to the compound corresponding to the INCI designation aphanothece sacrum polysaccharide modified by addition of thiol groups.

According to another particular embodiment, in solutions (A) and (B) implemented in the method according to the invention:

- Col-1 colloids are cerium dioxide colloids;
- the unsulfated polysaccharide is alginate;
- the source of bivalent metals, preferably an alkaline earth metal, is a calcium salt, preferably calcium carbonate;
- Col-2 colloids are platinum colloids with zero oxidation state, preferably platinum whose core exhibits zero oxidation state, surface and covalently bonded with cysteamine;

the acidifier is gluconolactone; and the sulfated polysaccharide corresponds to the compound corresponding to the INCI designation aphanothece sacrum polysaccharide.

According to the invention, after mixing the two solutions (A) and (B), the polymer networks are crosslinked and become entangled, without mutual interaction, forming a three-dimensional bipolymeric matrix in the form of a gel, with a plasticizing effect, which covers the lesion to be treated, maintaining a protective and breathable film around the lesion.

Preferably, the bipolymeric matrix according to the invention corresponds to a gel crosslinked by ionic bonds.

According to another aspect, the invention relates to a device for implementing the method according to the invention.

According to a particular embodiment, the two solutions (A) and (B) are packaged in a bottle, a sprayer, a syringe or a single-dose vial.

According to another particular embodiment, the two solutions (A) and (B) are packaged in a two-compartment container.

According to a particular embodiment, the device according to the invention is characterized in that:

solution (A) is at pH 7, and comprises Col-1 colloids non-covalently bonded to an unsulfated polysaccharide, a source of bivalent metals, preferably an alkaline earth metal, and Col-2 colloids covalently bonded with a biocompatible polymer; and solution (B) is at pH 3, and comprises an acidifier and a sulfated polysaccharide.

According to another particular embodiment, the device according to the invention is characterized in that:

solution (A) is at pH 7, and comprises Col-1 colloids non-covalently bonded to an unsulfated polysaccharide, a source of bivalent metals, preferably an alkaline earth metal, and Col-2 colloids covalently bonded with cysteamine; and solution (B) is at pH 3, and comprises an acidifier and a sulfated polysaccharide.

According to a particular embodiment, in solutions (A) and (B) implemented in the device according to the invention:

Col-1 colloids are cerium dioxide colloids;

the unsulfated polysaccharide is alginate;

the source of bivalent metals, preferably an alkaline earth metal, is a calcium salt, preferably calcium carbonate;

Col-2 colloids are platinum colloids with zero oxidation state, preferably platinum whose core exhibits zero oxidation state;

the biocompatible polymer is polyvinylpyrrolidone;

the acidifier is gluconic acid or gluconolactone, preferably gluconolactone; and the sulfated polysaccharide is the compound corresponding to the INCI designation aphanothece sacrum polysaccharide, modified by adding thiol groups.

Examples of two-compartment containers suitable for forming the matrix according to the invention are:

the two-compartment syringe sold by Doseurope and consisting of a double syringe of 42 ml volume, specifically designed for 4:1 ratios (product code: D-KART-050-04), of the static mixer L212 (product code: M-50-212) and a 4:1 double syringe gun (product code: PIST-50-4: 1); or the two-compartment Easymix Tube marketed by Neopac.

According to a preferred embodiment, in solutions (A) and (B) implemented in the device according to the invention:

Col-1 colloids are cerium dioxide colloids;

the unsulfated polysaccharide is alginate;

the source of bivalent metals, preferably an alkaline earth metal, is a calcium salt, preferably calcium carbonate;

Col-2 colloids are platinum colloids with zero oxidation state, preferably platinum whose core exhibits zero oxidation state, covalently bonded to cysteamine;

the acidifier is gluconolactone; and the sulfated polysaccharide is the compound corresponding to the INCI designation aphanothece sacrum polysaccharide.

The invention and the advantages resulting therefrom will emerge more clearly from the following figures and examples, given in order to illustrate the invention and not in a limiting manner.

FIG. 1 shows the diffractogram of $CeO_2$ colloids before non-covalently bonding with alginate.

FIG. 2 shows the diffractogram of Pt colloids before covalently bonding with aphanothece sacrum polysaccharide (INCI), modified by adding thiol groups.

FIG. 3 shows the degradation activity of ABTS (in %) of the bipolymeric matrix according to the invention compared to 2 commercial products, as a function of time (in minutes).

EXEMPLARY EMBODIMENTS OF THE INVENTION

1/Synthesis of Cerium Dioxide Colloids (Col-1) According to the Invention 0.1-2 mmol of dextrose or myo-inositol and 0.5-5 equivalents of a cerium dioxide precursor such as cerium chloride are dissolved in 10-100 mL of water. When dissolved, 1-10 equivalents of ammonia are added. The solution is kept under stirring for 1-5 h. Acetone is added as a counter solvent to allow purification by centrifugation. The pellet is redispersed in water at the desired concentration.

The result of this synthetic process is cerium dioxide colloids coated with dextrose or myo-inositol. In this complex, dextrose and myo-inositol perform a role of controlling the size of the particles and the narrow dispersion of the size of the particles around an average size.

2/Synthesis of Platinum Colloids (Col-2) According to the Invention, for Covalent Bonding with a Sulfated Polysaccharide A solution is prepared from 0.1 to 10 mmol of gluconolactone dissolved in 10 to 100 mL of water and then heated to reflux.

When reflux is reached, 0.01 to 10 mmol of a colloidal platinum precursor salt such as chloroplatinic acid and 0.001 to 1 mmol of polyvinylpyrrolidone (PVP), dissolved in 10 to 100 mL of water, are added to the reaction medium.

The solution is permitted to reflux for 1 to 5 hours.

The solution is then cooled to room temperature and acetone is added as a counter solvent to allow purification by centrifugation. The pellet is then dispersed to the desired concentration in the water.

The result of this synthetic process is platinum colloids dispersed in PVP. These colloids may be covalently bonded to a sulfated polysaccharide according to the invention, for example aphanothece sacrum polysaccharide (INCI), modified by adding thiol groups, the hemisynthesis of which is described in Example 3.

3/Hemi-Synthesis of Aphanothece Sacrum Polysaccharide (INCI), Modified by Adding Thiol Groups 10 to 100×10-7 mmol of aphanothece sacrum polysaccharide are dissolved in 10 to 100 mL of water and the solution is stirred.

100,000-100,000,00×10-7 mmol of N-(3-Dimethylaminopropyl)-N'-ethylcarbodiimide hydrochloride are added. The solution is kept under stirring for 10 to 100 min.

1,000,000 to 100,000,000×10-7 mmol of cysteine are added, the solution is kept under stirring until the solid dissolves. The pH is adjusted to 4.

The solution is kept under stirring for 6 to 24 hours. The pH is then adjusted to 6.

The solution is poured into approximately ten times its volume of ethanol in order to precipitate the aphanothece sacrum polysaccharide modified by adding thiol groups and recover this compound by centrifugation before dissolving it in a minimum of water (solution at 1-5% by mass) to be lyophilized.

4/Synthesis of Platinum Colloids (Col-2) According to the Invention, for Non-Covalent Bonding with the Sulfated Polysaccharide 0.1-10 mmol of gluconolactone is dissolved in 10-100 mL of water and the solution is heated to reflux.

When reflux is reached, 0.1-1 equivalent of a colloidal platinum precursor salt such as chloroplatinic acid and 0.01-0.1 equivalent of polyvinylpyrrolidone (PVP) dissolved in 10-100 mL of water are added to the reaction medium.

The solution is kept at reflux for 1-5 h. The solution is cooled to room temperature and 0.1-1 equivalent of cysteamine hydrochloride are added. The solution is kept under stirring for 1-5 hours and then acetone is added as a counter solvent to allow purification by centrifugation. The pellet is then dispersed to the desired concentration in the water.

The result of this synthetic process is platinum colloids modified by the addition of cysteamine and dispersed in PVP. These colloids may be non-covalently bonded (Coulomb interaction) to a sulfate polysaccharide, for example aphanothece sacrum polysaccharide (INCI).

5/$CeO_2$/Alginate and Pt/Aphanothece Sacrum Polysaccharide Colloids According to the Invention The small size of the $CeO_2$ and Pt particles makes it possible to have a larger area to cover and therefore to bond a greater number of molecules to the surface of each of the particles.

The diffractograms were measured on powder with an XRD of Cu-Kα source in transmission.

The diffractogram of $CeO_2$ colloids, before non-covalent bonding with alginate, is shown in FIG. 1.

The diffractogram of Pt colloids, before covalent bonding with aphanothece sacrum polysaccharide modified by addition of thiol groups, is shown in FIG. 2.

6/Manufacturing Process of the Bipolymeric Matrix According to the Invention

Two solutions (A) and (B) are mixed in a proportion of 4/5 of solution (A) and 1/5 of solution (B).

Solution (A) comprises $CeO_2$ colloids according to the invention, obtained from Example 1, and alginate, calcium carbonate, and Pt/aphanothece sacrum polysaccharide colloids according to the invention obtained from the mixture of reactions described in examples 2 and 3, and water;

Solution (B) includes native (unmodified) aphanothece sacrum polysaccharide (INCI) and gluconolactone dispersed in water.

Alternatively, solution A comprises $CeO_2$ colloids according to the invention, obtained from example 1, alginate, calcium carbonate, platinum colloids according to example 4 and native (unmodified) aphanothece sacrum polysaccharide (INCI) and water; and solution B of native (unmodified) aphanothece sacrum polysaccharide and gluconolactone dispersed in water.

After mixing, the three-dimensional bipolymeric matrix according to the invention is formed in a few minutes (1-5 minutes), or even seconds (less than a minute) by entanglement of the 2 crosslinked polymer networks according to the invention.

7/Determination of the Antioxidant Activity of the Three-Dimensional Bipolymeric Matrix According to the Invention The bipolymeric matrix according to the invention comprises:

- a quantity of Col-1 colloids non-covalently bonded with alginate which represents between 0.01 and 1% by weight of the matrix;
- a quantity of Col-2 colloids covalently bonded to aphanothece sacrum polysaccharide modified by addition of thiol groups, which represents between 0.001 and 0.1% by weight of the matrix;
- a quantity of water which represents between 70 and 99% by weight of the matrix.

A stock solution of ABTS (2,2'-azino-bis(3-ethylbenzothiazoline-6-sulphonic acid)) at 14 mM is incubated, at equal volume, with a 4.9 mM solution of a hydraulic solution of ammonium persulfate to produce a cationic ABTS radical. The reaction mixture is incubated in the dark for 16 hours at room temperature. The solution obtained is diluted to 1/100 with phosphate buffer (0.2 M, and pH 7.4) containing 150 mM of NaCl to obtain an absorbance of 1.5 at 734 nm.

Samples of different masses of between 1.2 and 12 mg of the three-dimensional bipolymeric matrix according to the invention are dispersed at 240 g/L in water and are added to 2970 μL of the cationic ABTS solution of 0.07 mM in water, then placed under stirring in the dark.

After 30 minutes of incubation, the ABTS is completely degraded.

The product is mixed with 3000 μL of the ABTS solution, as prepared above, in a polymethyl methacrylate ultraviolet (UV) spectrophotometry vessel. The reaction mixture is incubated in the dark for 30 minutes at room temperature. Then, the absorbance is measured every 20 minutes.

The antioxidant property of the bipolymeric matrix according to the invention is compared with two commercial products:

- the Nu-Gel® dressing corresponding to a hydrogel containing sodium alginate for the treatment of dry, fibrinous or necrotic sores;
- the Flaminal Hydro® dressing corresponding to a gel comprising alginate and an antimicrobial enzymatic system.

The data is shown in FIG. 3.

The results show that after 120 hours, approximately 85% of ABTS has been degraded by the bipolymeric matrix according to the invention, while the Nu-Gel® and Flaminal Hydro® dressings degrade approximately 18% and 27% of ABTS, respectively.

In conclusion, the antioxidant activity of the solution containing the bipolymeric matrix according to the invention is exponential and much greater compared to those of the 2 commercial dressings.

8/Determination of the Absorption Capacity of Exudates by the Three-Dimensional Bipolymeric Matrix According to the Invention The absorption capacity of exudates by the bipolymeric matrix according to the invention was compared with various commercial products indicated for the treatment of exudative or even very exudative sores.

An exudate solution is prepared by mixing 50 mL of fetal calf serum and 50 mL of a diluent containing 0.1% peptone and 0.9% sodium chloride. The sheet dressings are cut so as to obtain an area of 1.98 $cm^2$. The gel dressings are poured so as to cover an area of 1.98 $cm^2$.

Each sample is placed in a Petri dish 3 cm in diameter, then weighed (m0). Each dressing is covered with 4 mL of exudate before sealing the Petri dishes and storing them at 21° C. for 72 hours. The remaining exudate is removed from each dish and each sample is reweighed (ml).

The exudate absorption capacity of each dressing is determined according to the following formula:

$$\text{Absorption capacity} = \frac{m1 - m0}{m0} \times 100 \quad \text{[Math 1]}$$

The results are shown in Table 1 below.

TABLE 1

| Dressing brand | Permafoam Comfort | Biatain Adhesive | Intrasite Conformable | Hydrotac | Tegarderm Hydrocolloid Thin | Duoderm Extra Thin | Bipolymeric matrix according to the invention |
|---|---|---|---|---|---|---|---|
| Type | Hydrofiber | Hydrocellular | Hydrogel sheets | Hydrogel sheets | Hydrocolloid | Hydrocolloid | Hydrogel sheets |
| Absorption after 60 h (g/100 $cm^2$) | 66.25 | 101.60 | 11.64 | 35.41 | 19.81 | 30.90 | 15.36 |

The results show that the hydrofiber and hydrocellular type dressings, indicated for exudative or even very exudative sores, have better absorption with 65 to 100 g/$cm^2$ of exudate absorbed.

The hydrogel-type sheet dressings absorb 10-35 g/$cm^2$ of exudate.

Hydrocolloid-type dressings, indicated for the treatment of low-exudative sores, absorb between 20 and 30 g/$cm^2$ of exudate.

The bipolymeric matrix according to the invention absorbs 15 g/$cm^2$ of exudate, placing it in hydrogel-type sheet dressings. This is the only sheet hydrogel in liquid form to withstand the exudate absorption test, since the 2 commercial hydrogels evaluated (Intrasite Conformable and Hydrotac) partially or completely dissolved in the exudate.

This is explained by the crosslinking of the bipolymeric matrix according to the invention which allows the exudate to be absorbed while maintaining the shape of the dressing.

In addition, absorption of exudate occurs slowly, gradually, allowing rearrangement of the bipolymeric matrix. On the contrary, the commercial products tested absorb exudate like a sponge. As a result, after saturation, these products can no longer absorb exudate and are therefore no longer effective.

The invention claimed is:

1. A three-dimensional bipolymeric matrix exhibiting biomechanical activity, capable of neutralizing the various physiopathological parameters involved in the development and aggravation of skin lesions and/or sores combining:

a first polymeric network comprising first colloids (Col-1) non-covalently bonded to an unsulfated crosslinked polysaccharide, said first network being crosslinked by a bivalent metal; and a second crosslinked polymeric network comprising second colloids (Col-2), bonded covalently or non-covalently with a sulfated polysaccharide, said colloids (Col-2) being covalently bonded with an agent capable of positively charging the colloid;

and said matrix further comprising water and an acidifier.

2. The matrix according to claim 1, wherein the Col-1 colloids are cerium dioxide colloids and the unsulfated polysaccharide is selected from the group consisting of alginate, hyaluronic acid, guar gum, xanthan gum, acacia gum, pullulan, dextran and mixtures thereof.

3. The matrix according to claim 2, wherein the unsulfated polysaccharide is alginate.

4. The matrix according to claim 1, wherein the Col-2 colloids are platinum colloids and the sulfated polysaccharide is selected from the group consisting of a compound whose INCI designation is aphanothece sacrum polysaccharide, glycosaminoglycans sulphates, glucans, fucans, fucoidans, carrageenans, ulvans, pentosan polysulfate and mixtures thereof.

5. The matrix according to claim 4, wherein the sulfated polysaccharide is aphanothece sacrum polysaccharide.

6. The matrix according to claim 1, wherein the second colloids (Col-2) are non-covalently bonded to the sulfated polysaccharide.

7. A dressing to heal a skin sore comprising the matrix according to claim 1.

8. A method of healing a skin sore or radiodermatitis, said method comprising applying the matrix according to claim 1 to skin having thereon the skin sore or radiodermatitis.

9. The method according to claim 8, of healing a skin sore, wherein the skin sore is dry or exudative.

10. The method according to claim 8, of healing radiodermatitis, wherein the radiodermatitis is of dry to exudative grade.

11. A method of producing a three-dimensional bipolymeric matrix according to claim 1, wherein the matrix is obtained by mixing:

a solution (A) comprising Col-1 colloids non-covalently bonded with an unsulfated polysaccharide, a source of divalent metals, and Col-2 colloids covalently bonded at the surface with an agent capable of positively charging the colloid; and a solution (B) comprising an acidifier and a sulfated polysaccharide.

12. The method according to claim 11, wherein:

Col-1 colloids are cerium dioxide colloids;

the unsulfated polysaccharide is alginate;

the source of bivalent metals is a calcium salt;

Col-2 colloids are platinum colloids of zero oxidation state, covalently bonded at the surface with an agent capable of positively charging the colloid;

the acidifier is gluconolactone; and the sulfated polysaccharide is the compound corresponding to the INCI designation aphanothece sacrum polysaccharide.

13. The method according to claim 12, wherein:

the calcium salt is calcium carbonate, the Col-2 colloids are of platinum with a core of zero oxidation state, and the agent capable of positively charging the colloid is cysteamine.

14. The method according to claim 11, wherein the two solutions (A) and (B) are mixed in a proportion of 4/5 of solution (A) and 1/5 of solution (B).

15. The method according to claim 11, wherein the source of divalent metals is an alkaline earth metal and the agent capable of positively charging the colloid is cysteamine.

16. A device for implementing the method according to claim 11, said device comprising the solution (A) and the solution (B).

17. The device according to claim 16, wherein the solution (A) and the solution (B) are packaged in a bottle, a sprayer, a syringe or as a single dose vial.

18. The device according to claim 16, wherein the solution (A) and the solution (B) are packaged in a two-compartment container.

19. The device according to claim 16, wherein:

the solution (A) is at pH 7 and comprises Col-1 colloids non-covalently bonded to an unsulfated polysaccharide, a source of bivalent metals, and Col-2 colloids covalently bonded with an agent capable of positively charging the colloid; and the solution (B) is at pH 3, and comprises an acidifier and a sulfated polysaccharide.

20. The device according to claim 19, wherein:

Col-1 colloids are cerium dioxide colloids;

the unsulfated polysaccharide is alginate;

the source of bivalent metals is calcium carbonate;

Col-2 colloids are platinum colloids with zero oxidation state, which is platinum whose core exhibits zero oxidation state, covalently bonded to an agent capable of positively charging the colloid, which is cysteamine;

the acidifier is gluconolactone; and the sulfated polysaccharide is the compound corresponding to the INCI designation aphanothece sacrum polysaccharide.

* * * * *